United States Patent

Thies

[11] 4,016,176
[45] Apr. 5, 1977

[54] ESTERS OF 4-HYDROXY-2,9-DIOXATRICYCLO[4.3.1.0³,⁷] DECANES AND PROCESSES FOR THEIR PRODUCTION

[75] Inventor: Peter Willibrord Thies, Hannover, Germany

[73] Assignee: Kali-Chemie Pharma GmbH, Hannover, Germany

[22] Filed: Oct. 30, 1975

[21] Appl. No.: 627,081

Related U.S. Application Data

[63] Continuation-in-part of Ser. No. 440,038, Feb. 6, 1974, abandoned.

[30] Foreign Application Priority Data

Feb. 8, 1973  Germany ................ 2306118

[52] U.S. Cl. .................. 260/340.3; 424/278
[51] Int. Cl.² ....................... C07D 319/08
[58] Field of Search ................ 260/340.3

[56] References Cited

UNITED STATES PATENTS

| | | | |
|---|---|---|---|
| 3,185,692 | 5/1965 | Judd | 260/340.3 X |
| 3,324,000 | 6/1967 | Judd | 260/340.3 X |
| 3,455,912 | 7/1969 | Eitel et al. | 260/340.3 X |
| 3,917,651 | 11/1975 | Thies | 260/340.3 |

FOREIGN PATENTS OR APPLICATIONS

| | | | |
|---|---|---|---|
| 2,305,082 | 8/1973 | Germany | 260/340.3 |
| 1,961,433 | 6/1971 | Germany | 260/340.3 |

OTHER PUBLICATIONS

Finar, Fundamental Principles Organic Chemistry, p. 459.
Thies, Tetrahedron Letters, No. 35, pp. 3087–3090 (1970).

*Primary Examiner*—Ethel G. Love
*Attorney, Agent, or Firm*—Michael J. Striker

[57] ABSTRACT

Compounds consisting of esters of 4-hydroxy-2,9-dioxatricyclo[4.3.1.0³,⁷] decane having the formulae:

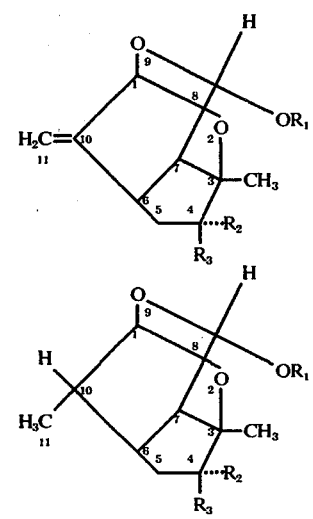

in which formulae $R_1$ is an alkyl radical having at most 4 carbon atoms, one of the radicals $R_2$ and $R_3$ is hydrogen and, when $R_2$ is a hydrogen radical, $R_3$ is a carbamyloxy radical and, when $R_3$ is a hydrogen radical, $R_2$ is a carbamyloxy, or an alkanoyl radical having at most 5 carbon atoms, the said carbamyloxy radical having the formula —OCONHR in which R is a hydrogen allyl, phenyl, cyclohexyl or an alkyl radical having at most 4 carbon atoms. The compounds are useful as sedatives and narcotics and can be produced by several different processes.

22 Claims, No Drawings

ESTERS OF 4-HYDROXY-2,9-DIOXATRICYCLO[4.3.1.0³,⁷] DECANES AND PROCESSES FOR THEIR PRODUCTION

CROSS-REFERENCE TO RELATED APPLICATION

This application is a continuation in part of our prior application Serial No. 440,038, filed February 6, 1974, now abandoned.

BACKGROUND OF THE INVENTION

Certain esters of 4-hydroxy-2,9-dioxatricyclo[4.3.1.0³,⁷]decanes are disclosed in published German Pat. application No. 1,961,433 and U.S. Pat. No. 3,812,154, in which the hydroxyl or acyloxy radical that is joined to the carbon atom numbered 4 and a β configuration. The radical is consequently represented as being attached to the carbon atom in the 4 position by a solid line, which differs from its epimer that is referred as having an α configuration and which is represented as being attached to the carbon atom in the 4 position by a dotted or broken line. These prior compounds possess nervous system depressant and vascular dilating activity and have the following formulae.

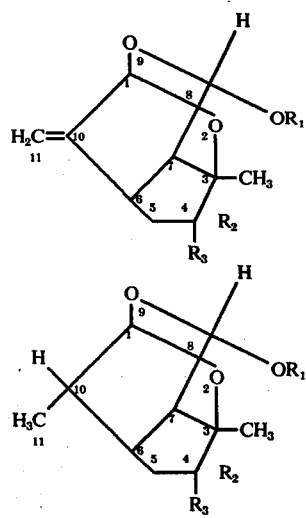

in which $R_2$ is hydrogen and $R_3$ is hydroxyl or an acyloxy radical.

SUMMARY OF THE INVENTION

It has now been discovered that esters of the epimers of the prior known derivatives of 4-hydroxy-2,9-dioxatricyclo[4.3.1.0³,⁷]decanes produce quickly and reliably, when administered intravenously, intraperitoneally, or orally, in doses that are only fractions of their toxic doses, a strong sedative or even a strong narcotic action. The action of the compounds of the present invention differs from that of known narcotics of this class in their effective dosage ranges by 1. more rapid onset of narcosis when administered orally,
2. lack of anticonvulsant activity,
3. rapid elimination and biodegradation after administration, and especially
4. absence of a depressant effect upon the vasomotor or respiratory system when doses are used which are capable of producing a narcosis lasting up to 1 hour, and
5. with respect to the compounds of this invention which have a double bond between the carbon atoms numbered 10 and 11, as in the second of the two foregoing formulae, absence of a boosting effect of barbiturates even after administration of narcotic doses of such compounds.

With small doses, the narcosis that is produced resembles a state of physiological sleep, from which the test animals can be awakened. The compounds of the present invention accordingly satisfy the requirements of an ideal hypnotic in conformity with the latest discoveries of investigations devoted to the nature of sleep.

Good oral resorbability and rapid onset of effectiveness are today also requirements of a hypnotic or sedative. No prior hypnotic or sedative is known which has the additional advantage of not boosting the effect of barbiturates. Of the great number of commercial narcotics, hypnotics, and sedatives, the barbiturates have the greatest share of the market and there is a real need for hypnotic, narcotic, and sedative compositions that contain no barbiturates.

Whereas the hydroxy and acyloxy radicals in the alcohols and esters described in published German Pat. application No. 1,961,433 have a β configuration with respect to the carbon atom numbered 4, the same radicals at the carbon atom numbered 4 in the compounds of the present invention have an α configuration. The epimeric compounds of the present invention produce changes not only in all physical characteristics but also drastic changes in their physiological reactions and effects.

The epimers can be produced for example by oxidation of the 4β-hydroxy derivatives that are described in published German patent application No. 1,961,433 to the 4-oxo derivatives (also known as 2,9-dioxatricyclo[4.3.1.0³,⁷]decane-4-ones) that are described in published German application No. 2,027,890, which have the formula:

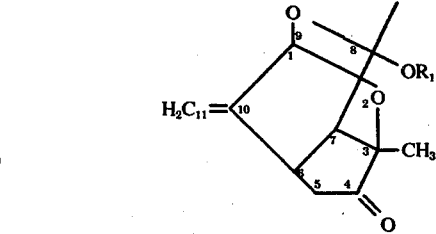

in which $R_1$ is an alkyl radical having at most 4 carbon atoms. The double bond between the carbon atoms numbered 10 and 11 can then be hydrogenated, followed by reduction, for example, with hydrogen in the presence of a Raney nickel catalyst, or preferably with a metal hydride, to produce a 4α-hydroxy derivative which is obtained in an amount equivalent to between 60 and 80% of the theoretical yield. The resulting 4α-hydroxy derivative can then be esterified in conventional manner with a carboxylic acid anhydride or carboxylic acid chloride. To produce the carbamate or 4α-carbamyloxy derivative, the 4α-hydroxy derivative is reacted with an isocyanate having the formula RNCO or with a carbamic acid ester or carbamic acid chloride having the formula RNCOR$_4$ in which formula R is a hydrogen, alkyl, phenyl, cyclohexyl or alkyl radical having at most 4 carbon atoms and R$_4$ is a chlorine or alkoxy radical.

It is also possible to react the 4α-hydroxy derivative with phosgene to produce the corresponding chloroformate and then react the chloroformate with a primary amine having the formula RNH$_2$ to obtain the desired carbamate.

The desired esters can also be produced by transesterification.

It has further been discovered that the 4β-carbamate derivatives of the 2,9-dioxatricyclo [4.3.1.0$^{3,7}$]decanes that are disclosed herein also have a greater sedative action than the 4β-esters that are disclosed in published German Pat. application No. 1,961,433. Particularly effective are the 4β-carbamate derivatives in which the carbamyloxy substitutent has the formula —OCONHR, in which formula R is an allyl, phenyl or cyclohexyl radical.

The 4β-carbamate derivatives of 2,9-dioxatricyclo[4.3.1.0$^{3,7}$]decanes can be prepared in a manner analogous to that used for the preparation of the 4α-carbamate derivatives by substituting for the 4α-hydroxy derivative a 4β-hydroxy-2,9-dioxatricyclo[4.3.1.0$^{3,7}$]decane derivative, such as is described in published German Pat. application No. 1,961,433, having the following formulae:

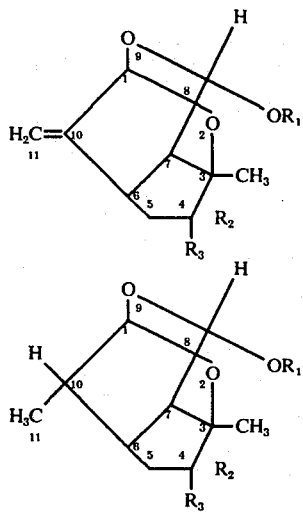

in which R$_1$ is an alkyl radical having at most 4 carbon atoms, R$_2$ is a hydrogen radical and R$_3$ is a hydroxyl radical.

DETAILED DESCRIPTION AND PREFERRED EMBODIMENTS OF THE INVENTION

The present invention is further described in the examples and tables which follow, which were selected solely for purposes of illustration and are consequently not to be construed as restrictive.

Compounds that have not been specifically disclosed in any of the examples are also included in the tables which follow the examples. The names and formulae of these compounds, which can be prepared analogously in accordance with the methods that are disclosed in the specific examples can be deduced from the data that are included in the tables.

In the examples and tables which follow, all melting points were determined with a Kofler block meltingpoint apparatus and are uncorrected and all specific optical rotations [α] are based upon a solution of 1 gram of the substance in 100 milliliters of methanol, unless otherwise specified.

EXAMPLE 1

4α-Hydroxy-8-methoxy-3-methyl-10-methylene-2,9-dioxatricyclo[4.3.1.0$^{3,7}$]decane (Compound No. 2090).

To a solution of 9.56 grams of 8-methoxy-3-methyl-10-methylene-2,9-dioxatricyclo [4.3.1.0$^{3,7}$]decane-4-one in 150 milliliters of dry diethyl ether contained in a flask provided with a stirrer and reflux condenser that is maintained under a blanket of nitrogen gas was added slowly with stirring a dispersion of 2.2 grams of lithium aluminum hydride (LiAlH$_4$, which is also known as lithium alanate) in 150 milliliters of dry diethyl ether. The mixture was heated for 1 hour at a reflux temperature, then cooled to 20° C and quenched in ice water. After the addition of ammonium sulfate the mixture was extracted with several portions of diethyl ether. The ether extracts were then combined, dried by contact with anhydrous sodium sulfate, decolorized with a small portion of animal charcoal, and filtered. The filtrate was then concentrated by removal of the diethyl ether by vacuum distillation, whereupon the residue crystallized. In this manner, 9.3 grams of crystals, corresponding to 96.4% of the theoretical yield of the compound that is designated herein as Compound No. 2090, which is also referred to by name in the heading of this example, was obtained. It had the formula and characteristics that are specified in Table 1 hereinafter.

EXAMPLE 2

4α-Acetoxy-8-methoxy-3-methyl-10-methylene-2,9-dioxatricyclo [4.3.1.0$^{3,7}$]decane (Compound No. 2117).

To a mixture of 2 milliliters of pyridine and 8 milliliters of acetic anhydride was added 3.2 grams of 4α-hydroxy-8-methoxy-3-methyl-10-methylene-2,9-dioxatricyclo [4.3.1.0$^{3,7}$]decane (Compound No. 2090) that was prepared as described in Example 1 hereinbefore and the resulting solution was allowed to stand at room temperature for a period of 24 hours. Subsequently the excess pyridine and acetic anhydride were separated by vacuum distillation and the residue was quenched in ice water and extracted with diethyl ether. After drying the combined ether extracts with anhydrous sodium sulfate and concentrating it by vacuum distillation, crystals of 4α-acetoxy-8-methoxy-3-methyl-10-methylene-2,9-dioxatricyclo [4.3.1.0$^{3,7}$]decane slowly crystallized therefrom. The crystals were separated by filtration and washed with a cold mixture of n-hexane and diethyl ether. In this manner 3.36 grams of the pure compound designated herein as Compound No. 2117, that is also referred to by name in the heading of this example, was obtained. This quantity corresponds to 87.6% of the theoretical yield and the compound has the formula and characteristics that are specified in Table 1 hereinafter.

EXAMPLE 3

4α-Propionyloxy-8-methoxy-3-methyl-10-methylene-2,9-dioxatricyclo[4.3.1.0$^{3,7}$]decane (Compound No. 2118).

By substituting 15 milliliters of propionic anhydride for the acetic anhydride in Example 2 and proceeding exactly as described in that example, 4.0 grams of the compound that is designated as Compound No. 2118 and is also referred to by name in the heading of this example, corresponding to 98.7% of the theoretical yield, was obtained. The compound had the formula and characteristics that are specified in Table 1 hereinafter.

EXAMPLE 4

4α-Isovaleryloxy-8-methoxy-3-methyl-10-methylene-2,9-dioxatricyclo[4.3.1.0$^{3,7}$]decane (Compound No. 2295).

By substituting an equivalent amount of isovaleric anhydride for the acetic anhydride in Example 2 and proceeding exactly as otherwise described in that example, the compound that is designated herein as Compound No. 2295 and is also referred to by name in the heading of this example was obtained. The compound had the formula and characteristics that are specified in Table 1 hereinafter.

EXAMPLE 5

4α-(N-Ethylcarbamyloxy)-8-methoxy-3-methyl-10-methylene-2,9-dioxatricyclo[4.3.1.0$^{3,7}$]decane, (Compound No. 2076).

To a solution of 5 grams of 4α-hydroxy-8-methoxy-3-methyl-10-methylene-2,9-dioxatricyclo[4.3.1.0$^{3,7}$]decane (Compound No. 2090), whose preparation is described in Example 1 hereinbefore, in 50 milliliters of dry benzene was added 2.5 milliliters of ethyl isocyanate and 3 drops of concentrated (95%) acetic acid and the mixture was heated and stirred for 1½ hours at a temperature of 60° C. After standing overnight at room temperature, the benzene was evaporated from the mixture by vacuum distillation and the residue was crystallized. The yield of the crude compound designated herein as Compound No. 2076 that is also referred to by name in the heading of this example was 6.7 grams, which corresponds to 99.5% of the theoretical yield. The compound was recrystallized from a mixture of diethyl ether and n-hexane and had the formula and characteristics that are specified in Table 1 hereinafter.

The toxicity and narcotic effectiveness of this compound were determined in tests with cats and dogs. The lethal dose (LD$_{50}$) for cats determined by intravenous administration was 226 milligrams per kilogram of body weight. The intravenous administration of a dose equivalent to 5 milligrams per kilogram of body weight to cats produced a narcosis that persisted for 10 minutes, whereas doses of 10 and 15 milligrams per kilogram produced narcoses that persisted for 25 and 60 minutes, respectively.

In dogs a dose of 17.5 milligrams of the compound per kilogram of body weight administered intravenously was required to produce a narcosis that persisted for 1 hour.

EXAMPLE 6

4β-(N-Isopropylcarbamyloxy)-3,10-dimethyl-8-methoxy-2,9-dioxatricyclo[4.3.1.0$^{3,7}$]decane (Compound No. 2057).

To a solution of 10 milliliters of isopropyl isocyanate in 50 milliliters of benzene were added 4.5 grams of 4β-hydroxy-3,10-dimethyl-8-methoxy-2,9-dioxatricyclo[4.3.1.0$^{3,7}$]decane, which is designated Compound No. 1246 herein and has the formula and characteristics that are specified in Table 1 hereinafter, and which can be prepared by the procedures described in Examples 2 and 3 of published German patent application No. 1,961,433. After the addition of 5 drops of concentrated (95%) acetic acid to the resulting clear solution, it was allowed to stand at room temperature for a period of 24 hours. Subsequently the excess isopropyl isocyanate was evaporated from the mixture by vacuum distillation during which additional portions of benzene were added. The residue was quenched in ice water and extracted with benzene. After washing the benzene extracts with water, they were dried over anhydrous sodium sulfate and concentrated by vacuum distillation. A yellow-colored oil was obtained which, upon trituration with a mixture of diethyl ether and n-hexane, formed crystals. There was thus obtained 4.7 grams, equivalent to a yield of 75% of the theoretical, of the compound designated herein as Compound No. 2057 that has the formula and characteristics that are specified in Table 2 hereinafter, which is also referred to by name in the heading of this example.

EXAMPLE 7

4α-Hydroxy-8-methoxy-3,10-dimethyl-2,9-dioxatricyclo[4.3.1.0$^{3,7}$]decane (Compound No. 1561).

In accordance with the procedure described in Example 1, 4.0 grams of 3,10-dimethyl-8-methoxy-2,9-dioxatricyclo [4.3.1.0$^{3,7}$]decane-4-one, which was prepared in accordance with the method described in Example 2 of published German patent application No. 2,027,890, was treated with lithium aluminum hydride in dry diethyl ether. There was thus obtained 4.0 grams, which is equivalent to a substantially quantitative yield, of 4α-hydroxy-8-methoxy-3,10-dimethyl-2,9-dioxatricyclo[4.3.1.0$^{3,7}$]decane, which was designated herein as Compound No. 1561 and has the formula and characteristics that are specified in Table 2 hereinafter.

EXAMPLE 8

4α-Acetoxy-8-methoxy-3,10-dimethyl-2,9-dioxatricyclo[4.3.1.0$^{3,7}$]decane (Compound No. 2080).

To a mixture of 4 milliliters of pyridine and 12 milliliters of acetic anhydride was added 4.0 grams of the 4α-hydroxy-8-methoxy-3,10-dimethyl-2,9-dioxatricyclo[4.3.1.0$^{3,7}$]decane (Compound No. 1561) that was prepared in accordance with the procedure described in Example 7 and the clear solution was allowed to stand for 4 hours at room temperature. The pyridine and excess acetic anhydride were then evaporated from the mixture by vacuum distillation and the residue was quenched in ice water and extracted with diethyl ether. The extract was then washed successively with a 1-normal aqueous solution of sodium hydroxide, dried by contact with anhydrous sodium sulfate, and evaporated by vacuum distillation until the residue had reached a constant weight. There was thus obtained 4.5 grams, equivalent to 94% of the theoretical yield, of the compound designated herein as Compound No. 2080 that is also referred to by name in the subject heading, which has the formula and characteristics specified in Table 2 hereinafter.

EXAMPLE 9

4α-Isovaleryloxy-8-methoxy-3,10-dimethyl-2,9-dioxatricyclo[4.3.1.0$^{3,7}$]decane (Compound No. 2215).

By substituting an equivalent amount of isovaleric anhydride for the acetic anhydride in Example 8 and proceeding exactly as otherwise described in that example, the compound that is designated herein as Compound No. 2215 and is also referred to by name in the heading of this example, was obtained. The compound had the formula and characteristics that are specified in Table 2.

Both of the foregoing Compounds Nos. 2080 and 2215 that are described in Example 8 and 9 can also be produced by catalytic reduction of respectively 4α-acetoxy and 4α-isovaleryloxy-8-methoxy-3-methyl-10-methylene-2,9-dioxatricyclo[4.3.1.0$^{3,7}$]decanes that can be obtained in accordance with the process described in Example 2 hereinbefore, for example, by catalytic reduction with hydrogen in the presence of a palladium catalyst supported on a charcoal carrier, as described in Example 3 of published German patent application No. 1,961,433.

EXAMPLE 10

4α-(N-Ethylcarbamyloxy)-8-methoxy-3,10-dimethyl-2,9-dioxatricyclo[4.3.1.0$^{3,7}$]decane (Compound No. 2026).

To a solution in benzene of 5.0 grams of 4α-hydroxy-8-methoxy-3,10-dimethyl-2,9-dioxatricyclo[4.3.1.0$^{3,7}$]decane (Compound No. 1561) prepared as described in Example 7 was added 5 milliliters of ethyl isocyanate and 3 drops of concentrated (95%) acetic acid as catalyst. After several hours the conversion of the alcohol to the corresponding carbamate proceeded substantially to completion. The mixture was then neutralized with sodium bicarbonate, washed with water and, after drying, the benzene phase was evaporated by vacuum distillation, to leave a residue consisting of a white crystalline mass. The yield of the compound designated herein as 2026 which is also referred to by name in the heading of this example, and whose formula and characteristics are specified in Table 2 hereinafter, was substantially quantitative.

EXAMPLE 11

4β-Carbamyloxy-8-methoxy-3-methyl-10-methylene-2,9-dioxatricyclo[4.3.1.0$^{3,7}$]decane (Compound No. 2230).

A mixture of 6.0 grams of 4β-hydroxy-8-methoxy-3-methyl-10-methylene-2,9-dioxatricyclo[4.3.1.0$^{3,7}$]decane designated Compound No. 981 herein, whose preparation is described in Example 1 of published German patent application No. 1,961,433 and in Example 3 of our United States patent No. 3,812,154, 7.0 grams of urethane(NH$_2$COOC$_2$H$_5$) and 0.4 gram of aluminum isopropoxide was heated at a temperature between 150° and 154° C and at a subatmospheric pressure of 200 torrs for a period of 5 hours while ethanol that was evolved during the reaction was collected. The end of the reaction was established by the amount of ethanol that had been collected. Toward the end of the reaction the greater proportion of the excess urethane was distilled off after the distillation pressure was further reduced to approximately 50 torrs. There was thus obtained a very viscous yellow-colored residue which was purified chromatographically in a silica gel column and the desired carbamate, designated herein as Compound No. 2230, which is also referred to by name in the subject heading, and whose formula and characteristic are specified in Table 1 hereinafter, was crystallized from a mixture of ethanol and carbon tetrachloride. The yield of the compound was 87.3% of the theoretical.

EXAMPLE 12

4α-(N-Allylcarbamyloxy)-8-methoxy-3-methyl-10-methylene-2,9-dioxatricyclo[4.3.1.0$^{3,7}$]decane (Compound No. 2286).

A solution of 5.0 grams of 4α-hydroxy-8-methoxy-3-methyl-10-methylene-2,9-dioxatricyclo[4.3.1.0$^{3,7}$]decane (Compound No. 2090) prepared as described in Example 1 and 6.5 grams of allyl isocyanate in 70 milliliters of dry benzene was heated for 24 hours under gentl reflux. The mixture was then subjected to vacuum distillation and, in order to remove the excess allyl isocyanate, 50 milliliters of ethanol was added to the residue and the mixture was again subjected to vacuum distillation. To the residue was then added 150 milliliters of water and the resulting mixture was then extracted four times with 100-milliliter portions of diethyl ether. The combined ether extracts were then combined and dried by contact with anhydrous magnesium sulfate, decolorized with a small amount of animal charcoal, filtered, and the filtrate was subjected to vacuum distillation. In this manner, 7.5 grams of a crude crystalline product was obtained. When this crude product was recrystallized from a mixture of diethyl ether and n-hexane in the ratio of 1 volume of diethyl ether to 9 volumes of n-hexane, 4.5 grams of white crystals, equivalent to a yield of 71.5% of the theoretical, was obtained. The crystals had a melting point of 98°–101° C and a specific optical rotation $[\alpha]_D^{23}$ of +38°. The elementary analysis of the compound conformed to the empirical formula C$_{15}$H$_{21}$NO$_5$. This compound is designated herein as Compound No. 2286 and is also referred to by name in the heading of this example. Its formula and characteristics are also specified in Table 1 hereinafter.

EXAMPLE 13

4α-(N-Allylcarbamyloxy)-8-methoxy-3-methyl-10-methylene-2,9-dioxatricyclo[4.3.1.0$^{3,7}$]decane (Compound No. 2306).

In accordance with the procedure described in Example 12, 5.0 grams of 4β-hydroxy-8-methoxy-3-methyl-10-methylene-2,9-dioxatricyclo[4.3.1.0$^{3,7}$]decane which was referred to in Example 6 and is designated Compound No. 1246 herein, was reacted with allyl isocyanate in benzene to produce 7.5 grams of a crude oily product. When this crude product was subjected to chromatographic separation in a column containing 100 grams of silica gel using as eluting agent a mixture of carbon tetrachloride and chloroform in the ratio of 80 volumes of carbon tetrachloride to 20 volumes of chloroform, 5.0 grams of white crystals, equivalent to a yield of 79.3% of the theoretical, was obtained. The crystals had a melting point of 52°–53° C and a specific optical rotation $[\alpha]_D^{23}$ of +46°. The elementary analysis of the compound conformed to the empirical formula C$_{15}$H$_{21}$NO$_5$.

EXAMPLE 14

4α-(N-Allylcarbamyloxy)-8-methoxy-3,10-dimethyl-2,9-dioxatricyclo[4.3.1.0$^{3,7}$]decane (Compound No. 2274).

A solution in benzene of 4.5 grams of 4α-hydroxy-8-methoxy-3,10-dimethyl-2,9-dioxatricyclo[4.3.1.0$^{3,7}$]-decane, which was designated herein as Compound No. 1561 and whose preparation is described in Example 7 hereinbefore, and 4.0 grams of allyl isocyanate to which 3 drops of concentrated (95%) acetic acid was added was heated at a temperature between 50 and 60° C for a period of 24 hours. The reaction product was recovered and recrystallized in accordance with the general procedure described in Example 12 hereinbefore. After recrystallization of the crude product which weighed 6.0 grams from a mixture of n-hexane and diethyl ether in the ratio of 9 volume of n-hexane to 1 volume of diethyl ether, 4.2 grams of pure white crystals was obtained, equivalent to 67% of the theoretical yield. The crystals had a melting point of 56°–58° C and a specific optical rotation $[\alpha]_D^{22}$ of $-32°$. The elementary analysis of the compound conformed to the empirical formula $C_{15}H_{23}NO_5$. This compound is designated herein as Compound No. 2274 and is also referred to by name in the heading of this example. Its formula and characteristics are also specified in Table 2 hereinafter.

EXAMPLE 15

4α-(N-Cyclohexylcarbamyloxy)-8-methoxy-3,10-dimethyl-2,9-dioxatricyclo[4.3.1.0$^{3,7}$]decane (Compound No. 2365).

A solution in 70 milliliters of benzene of 5.0 grams of 4α-hydroxy-8-methoxy-3,10-dimethyl-2,9-dioxatricyclo[4.3.1.0$^{3,7}$]decane, which is designated Compound No. 1561 herein and whose preparation is described in Example 7 hereinbefore and 5.0 grams of cyclohexyl isocyanate to which 3 drops of concentrated (95%) acetic acid was added, was heated under reflux for a period of 6 hours. The reaction product was recovered as a crude oil in accordance with the general procedure described in Example 4 and was recrystallized from n-hexane. The yield was 6.2 grams of white crystals which is equivalent to 78% of the theoretical. The crystals had a melting point of 109°–110° C and a specific optical rotation $[\alpha]_D^{21}$ of $-26°$. The elementary analysis of the compound conformed to the empirical formula $C_{18}H_{29}NO_5$. This compound is designated herein as Compound No. 2365 and is also referred to by name in the heading of this example. Its formula and characteristics are also specified in Table 2 hereinafter.

EXAMPLE 16

4α-(N-Cyclohexylcarbamyloxy)-8-methoxy-3-methyl-10-methylene-2,9-dioxatricyclo[4.3.1.0$^{3,7}$]decane (Compound No. 2365).

A solution in benzene of 6.5 grams of 4α-hydroxy-8-methoxy-3-methyl-10-methylene-2,9-dioxatricyclo[4.3.1.0$^{3,7}$]decane, which is designated Compound No. 2090 herein and whose preparation is described in Example 1, and 15 grams of cyclohexyl isocyanate was reacted in accordance with a procedure analogous to that described in Example 4 hereinbefore and recovered as described therein. Since the product could not be crystallized, it was purified by chromatography on 17 thick plates of silica gel having a surface dimension of 20 × 20 centimeters using as eluting solvent a mixture of n-hexane, ethyl acetate and n-propanol in the ratio of 70 volumes of n-hexane to 24 volumes of ethyl acetate and 6 volumes of n-propanol. In this manner, 5.5 grams of a colorless oil, which was equivalent to 59% of the theoretical yield, was obtained. This oil had a specific optical rotation $[\alpha]_D^{21}$ of $+62°$. The elementary analysis of the product conformed to the empirical formula $C_{18}H_{27}NO_5$.

EXAMPLE 17

4β-(N-Phenylcarbamyloxy)-8-methoxy-3,10-dimethyl-2,9-dioxatricyclo[4.3.1.0$^{3,7}$]decane.

A solution in 200 millimeters of benzene of 3.4 grams of 4β-hydroxy-8-methoxy-3,10-dimethyl-2,9-dioxatricyclo[4.3.1.0$^{3,7}$]decane whose preparation is described in Example 2 of published German patent application No. 1,961,433 and 5.13 grams of phenyl isocyanate to which was added 10 drops of concentrated (95%) acetic acid was heated for 15 minutes at a temperature of 60°C. The mixture was then cooled and allowed to stand at room temperature for 24 hours. Subsequently, the mixture was concentrated by vacuum distillation of the solvents therefrom and the product was recovered in a manner analogous to that described in Example 12. After recrystallization from benzene, 4.1 grams of white crystals was obtained, which is equivalent to 79% of the theoretical yield. These crystals had a melting point of 154°–156° C and a specific optical rotation $[\alpha]_D^{20}$ of $+17°$. The elementary analysis of the compound conformed to an empirical formula of $C_{18}H_{23}NO_5$.

The compound thus prepared did not produce narcosis, yet it has an effect on the nervous system and, in experiments with white mice, was effective as a muscle relaxant (similar to the action of phenobarbital) and spasmolytic ($ED_{50} = 0.1\%$ of the $ED_{100}$ of papaverine and 0.2% of the $ED_{100}$ of atropine; $LD_{50}$ of the compound = 1500mg/kg p.o.).

The formulae, melting points and specific optical rotations $[\alpha]_D^{20}$ of most of the compounds disclosed in the foregoing examples as well as other analogous compounds are included in Tables 1 and 2 which follow. The numbers in brackets after the number of the compound refers to the example in which the preparation of the particular compound was described.

The carbamic acid esters that are listed in the tables were produced by reacting 4α or 4β-hydroxy-8-alkoxy-3-methyl-10-methylene-2,9-dioxatricyclo[4.3.1.0$^{3,7}$]decanes or 4α or 4β-hydroxy-8-alkoxy-3,10-dimethyl-2,9-dioxatricyclo[4.3.1.0$^{3,7}$]decanes with the corresponding isocyanates as described in Examples 4, 6 and 10 to 17 hereinbefore.

TABLE 1

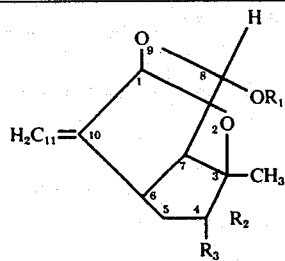

| Compound No. | $R_1$ | $R_2$ | $R_3$ | m.p., °C | $[\alpha]_D^{20}$ |
|---|---|---|---|---|---|
| 981 | $CH_3$ | H | OH | oil | +42° |
| 2090 [1] | $CH_3$ | OH | H | 63 | +30° |
| 2009 | $CH_3$ | H | $OCOCH_3$ | 55 | +69° |
| 2117 [2] | $CH_3$ | $OCOCH_3$ | H | 58 | +33° |
| 2043 | $CH_3$ | H | $OCOC_2H_5$ | oil | +70° |
| 2118 [3] | $CH_3$ | $OCOC_2H_5$ | H | 51–53 | +39° |
| 2067 | $CH_3$ | H | $OCONHC_2H_5$ | 77–79 | +54° |
| 2076 [5] | $CH_3$ | $OCONHC_2H_5$ | H | 123–124 | +30° |
| 2166 | $CH_3$ | $OCONHCH(CH_3)_2$ | H | oil | +33° |
| 2199 | $CH_3$ | H | $OCOCH_2CH(CH_3)_2$ | oil | +49° |
| 2179 | $C_2H_5$ | $OCONHC_2H_5$ | H | oil | +17° |
| 2230 [11] | $CH_3$ | H | $OCONH_2$ | 142 | +42° |

| | | | | | $[\alpha]_D^{23}$ |
|---|---|---|---|---|---|
| 2286 [12] | $CH_3$ | $OCONHCH_2CH=CH_2$ | H | 98–101 | +38° |
| 2219 | $CH_3$ | $OCONHC(CH_3)_3$ | H | 162 | +53° |
| 2241 | $C_2H_5$ | H | $OCONHC_2H_5$ | oil | +55° |
| 2249 | $C_2H_5$ | $OCONHCH(CH_3)_2$ | H | oil | +52° |
| 2295 [4] | $CH_3$ | $OCOCH_2CH(CH_3)_2$ | H | 58 | +41° |
| 2309 | $CH_3$ | H | $OCONH(CH_2)_3CH_3$ | oil | +37° |
| 2388 | $CH_3$ | $OCONHCH_2CH_2CH_3$ | H | 51–53 | +35° |
| 2390 | $CH_3$ | H | $OCONHCH_2CH_2CH_3$ | oil | +53° |
| 2400 | $CH_3$ | H | $OCONHC_6H_{11}$ | oil | +36° |
| 2418 | $CH_3$ | $OCONH_2$ | H | 184 | +48° |
| 2448 | $CH_3$ | H | $OCONHC_6H_5$ | 80–83 | +35° |
| 2504 | $CH_3$ | $OCONHCH_3$ | H | 145–148 | +28° |
| 2609 | $C_2H_5$ | $OCONHCH_3$ | H | 183–185 | +52° |
| 2611 | $CH_3$ | H | $OCONHCH_3$ | oil | +82° |
| 2531 | $CH_2CH(CH_3)_2$ | $OCONH(CH_2)_2CH_3$ | H | oil | +35° |
| 2532 | $CH_2CH(CH_3)_2$ | $OCONHCH_3$ | H | 126–128 | +39° |
| 2538 | $CH_2CH(CH_3)_2$ | H | $OCONHCH_3$ | oil | +58° |
| 2582 | $CH_3$ | $OCONHC_6H_5$ | H | oil | +42° |
| 2612 | $CH_3$ | H | $OCONHC(CH_3)_3$ | oil | +45° |
| 2658 | $C_2H_5$ | $OCONHCH_2-CH=CH_2$ | H | oil | +56° |

TABLE 2

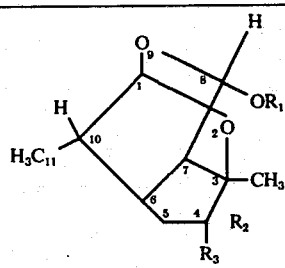

| Compound No. | $R_1$ | $R_2$ | $R_3$ | m.p., °C | $[\alpha]_D^{20}$ |
|---|---|---|---|---|---|
| 1246 | $CH_3$ | H | OH | oil | −36° |
| 1561 [7] | $CH_3$ | OH | H | oil | −61° |
| 2045 | $CH_3$ | H | $OCOCH_3$ | oil | 0° |
| 2080 [8] | $CH_3$ | $OCOCH_3$ | H | oil | −35° |
| 2044 | $CH_3$ | H | $OCOC_2H_5$ | 49–52 | 0° |
| 2081 | $CH_3$ | $OCOC_2H_5$ | H | oil | −32° |
| 1767 | $CH_3$ | H | $OCONHC_2H_5$ | 91–93 | −2° |
| 2026 [10] | $CH_3$ | $OCONHC_2H_5$ | H | 103–105 | −31° |
| 2057 [6] | $CH_3$ | H | $OCONHCH(CH_3)_2$ | 128–132 | 0° |
| 2065 | $CH_3$ | $OCONHCH(CH_3)_2$ | H | oil | −27° |
| 2190 | $CH_3$ | H | $OCONH_2$ | 130 | −5° |
| 2157 | $C_2H_5$ | $OCONHC_2H_5$ | H | 73–75 | −17° |

| | | | | | $[\alpha]_D^{22}$ |
|---|---|---|---|---|---|
| 2274 [14] | $CH_3$ | $OCNHCH_2CH=CH_2$ | H | 56–58 | −32° |
| 2046 | $CH_3$ | $OCONHC_6H_5$ | H | oil | −23° |
| 2239 | $C_2H_5$ | $OCONHC_6H_5$ | H | oil | −16° |
| 2212 | $CH_3$ | H | $OCOCH_2CH(CH_3)_2$ | oil | ±0 |
| 2215 [9] | $CH_3$ | $OCOCH_2CH(CH_3)_2$ | H | oil | −14° |

TABLE 2-continued

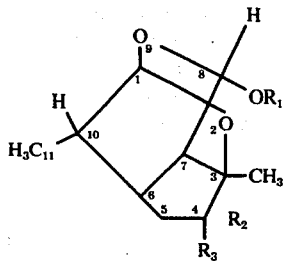

| Compound No. | $R_1$ | $R_2$ | $R_3$ | m.p., °C | $[\alpha]_D^{20}$ |
|---|---|---|---|---|---|
| 2252 | $CH_3$ | $OCONH_2$ | H | 157-158 | -39° |
| 2327 | $CH_3$ | $OCONH(CH_2)_3CH_3$ | H | oil | -23° |
| 2328 | $CH_3$ | $OCONHC(CH_3)_3$ | H | oil | -27° |
| 2356 | $CH_3$ | H | $OCONHC(CH_3)_3$ | 143-145 | ±0 |
| 2357 | $CH_3$ | H | $OCONH(CH_2)_3CH_3$ | oil | ±0 |
| 2364 | $CH_3$ | $OCONHCH_2CH_2CH_3$ | H | oil | -20° |
| 2427 | $CH_3$ | H | $OCONHCH_2-CH=CH_2$ | oil | ±0 |
| 2500 | $CH_3$ | $OCONHCH_3$ | H | 82-83 | -24° |
| 2607 | $C_2H_5$ | $OCONHCH_3$ | H | 128-130 | -34° |
| 2650 | $CH_3$ | H | $OCONHCH_3$ | oil | +27° |
| 2652 | $C_2H_5$ | H | $OCONHCH_3$ | oil | ±0 |
| 2675 | $CH_3(CH_2)_3$ | $OCONHC_2H_5$ | H | oil | -13° |
|  |  |  |  |  | $[\alpha]_D^{21}$ |
| 2365 [15] | $CH_3$ | $OCONHC_6H_{11}$ | H | 109-110 | -26° |

DETAILED DESCRIPTION OF UTILITY

In the Table 3 which follows are listed results of tests pertaining to the effectiveness of various compounds that are disclosed herein. The results are included in the several columns under letters whose significance is as follows:

A - Lethal dose ($LD_{50}$) to mice in milligrams per kilogram of body weight of the mouse when administered per os.

B - Lethal dose ($LD_{50}$) to mice in milligrams per kilogram of body weight of the mouse when administered intraperitoneally.

C - Ataxia: Dose in milligrams per kilogram of body weight required to produce ataxia in a mouse.

D - Narcosis (lateral position): The dose ($ED_{50}$) in milligrams per kilogram of body weight which produces narcosis for 3 minutes in 50% of the mice tested when administered intraperitoneally.

E - The dose in milligrams per kilogram of body weight which prolongs narcosis produced by hexobarbital in a mouse by a factor of 4.

The dashes in the table indicate that no effect was observed in dosage ranges below the toxic doses of each compound.

TABLE 3

| Compound No. | A | B | C | D | E |
|---|---|---|---|---|---|
| 981 | 610 | 600 | 200 | — | 100 |
| 2090 [1] | 774 | 300 | 25 | <300 | — |
| 2067 | 872 | 390 | 50 | — | 215 |
| 2076 [5] | 1025 | 527 | 50 | <100 | — |
| 2179 | 944 | 802 | <100 | <100 | — |
| 2157 | 1470 | 527 | — | 100 | — |
| 1246 | >1500 | 1200 | 800 | — | 68 |
| 1561 [7] | >1500 | 1600 | 200 | 800 | 68 |
| 2045 | 1470 | 1000 | 200 | — | 316 |
| 2080 [8] | >1470 | >1000 | 50 | — | — |
| 2044 | 1470 | 436 | 147 | — | — |
| 2081 | >1470 | 1379 | 50 | — | 316 |
| 2057 [6] | >1470 | 1000 | 147 | — | — |
| 2065 | 156 | 118 | 12 | 46.4 | 31.6 |
| 1767 | >1500 | 890 | 400 | 0 | 0 |

TABLE 3-continued

| Compound No. | A | B | C | D | E |
|---|---|---|---|---|---|
| 2026 [10] | 518 | 297 | 68.1 | 100 | 31.6 |

Interference with muscular coordination, that is, ataxia, narcosis and the prolongation of narcosis produced by hexobarbital were selected as criteria for a sedative and hypnotic effect since they are readily observed and estimated.

Comparison, for example, of the epimeric Compounds Nos. 2067 and 2076 (respectively 4β and 4α-(N-ethylcarbamyloxy)-8-methoxy-3-methyl-10-methylene-2,9-dioxatricyclo[4.3.1.0$^{3,7}$]decanes) with each other, reveals that, although both compounds have substantially the same toxicity and identical doses are effective in producing ataxia, only Compound No. 2076 (the α epimer) produces narcosis but does not prolong narcosis produced by hexobarbital, whereas Compound No. 2067 (the β epimer) does not produce narcosis yet prolongs narcosis produced by hexobarbital.

These differences are even more pronounced in the case of the hydrogenated analogues, namely, Compounds Nos. 2057 and 2065. Compound No. 2057 (the β epimer) produces neither a narcosis nor a prolongation of narcosis produced by hexobarbital, whereas Compound No. 2065 (the α epimer) produces a very strong narcosis as well as prolongation of narcosis produced by hexobarbital.

Furthermore, whereas 147 milligrams per kilogram of body weight of Compound No. 2057 is required for producing ataxia, only 12 milligrams per kilogram of Compound No. 2065 is required for the same purpose. This ten-fold increase in effectiveness in producing ataxia is also accompanied by an increase in the toxicity, but the ratio between effective and lethal doses nonetheless remains constant.

When the effective doses of the 4β-hydroxy compounds that produce ataxia are compared with those of the 4β-esters in Table 3, it will be noted that esterification produces a distinct increase in the sedative effect or ataxia with a simultaneous reduction in the relative toxicity, for example, with the esters of acetic, propionic, ethylcarbamic, and isopropylcarbamic acids (compare Compounds Nos. 2045, 2044, 1767 and 2057 with Compound No. 1246). An increase in their effectiveness as narcotics is not attained although the esters are significantly more lipophilic than the alcohols from which each is derived.

The effectiveness of the 2,9-dioxatricyclo[4.3.1.0$^{3,7}$]-decanes of the present invention as narcotics is obviously sterospecifically related to the 4α-configuration. This is clearly apparent from a comparison of the pairs of epimers which are listed in Table 3. Particularly surprising is the narcotic effect of the esters as compared to the 4-hydroxy compounds. Whereas nearly 300 or even 800 milligrams per kilogram of the 4-hydroxy compounds are required to induce narcosis, the required doses of the carbamates is only at most 100 milligrams per kilogram and their toxicity is in general very low. The esters show in general a greater sedative effect than the corresponding hydroxy compounds which is particularly remarkable when comparing Compound No. 1561 with Compounds Nos. 2080, 2081 and 2026.

The sedative and hypnotic effectiveness of the compounds of the invention were also ascertained by screening tests with white mice described by Campbell and Richter in Acta Pharmacol. et Toxicol. 25 (1967) page 345. In Table 4 the results of various specific screening tests are listed. These tests were as follows:
A. Lethal dose (LD$_{50}$) to mice in milligrams per kilogram body weight of the mouse when administered per os.
B. Lethal dose (LD$_{50}$) to mice in milligrams per kilogram body weight of the mouse administered intraperitoneally.
F. Ptosis test
G. Reduced motility test.
H. Lateral position narcosis test.
I. Haffner reflex failure.
J. Climbing test (ED$_{50}$).
K. Balance bar test (ED$_{50}$).

The values specified in Tables 4 and 5 hereinafter refer to milligrams per kilogram of body weight of the mouse.

TABLE 4

| Compound No. | A | B | F | G | H | I | J | K |
| --- | --- | --- | --- | --- | --- | --- | --- | --- |
| 2388 | 619 | 516 | 100 | 100 | 100 | 200 | 75 | 33 |
| 2286 [12] | 970 | 444 | 50 | 50 | 50 | 100 | 112 | 50 |
| 2364 | 327 | 244 | 100 | 50 | 100 | 100 | 44 | 38 |
| 2274 [14] | 339 | 279 | 100 | 25 | 100 | 100 | 75 | 62.5 |
| 2504 | 528 | 492 | — | — | 125 | — | — | 200 |
| 2658 | 470 | 331 | — | — | 200 | — | 185 | 62 |
| 2327 | 690 | 432 | 100 | 50 | 100 | 100 | 56 | 18 |
| 2328 | 1470 | 1131 | 200 | 100 | 200 | 400 | 175 | 56 |
| 2365 [15] | 1470 | 832 | 400 | 200 | 400 | 400 | 150 | 137 |
| 2500 | 1143 | 954 | 400 | 100 | 100 | 400 | 250 | 621 |

Tests performed in accordance with the procedure described by Campbell and Richter in Acta Pharmacol. et Toxicol., vol. 25, page 345 (1967), also showed that an increase in the sedative effectiveness could be achieved by esterification of the 4-hydroxyl group of the 2,9-dioxatricyclo[4.3.1.0$^{3,7}$]decanes to which the present invention pertains. This is indicated by the results that are reported in Table 5 in which the headings A and F have the same significance as hereinbefore while the values in the column heading L pertain to the dose in milligrams per kilogram of body weight that was required to produce a lowering of the rectal temperature, which are values indicative of the depressant effect of a compound upon the central nervous system.

TABLE 5

| Compound No. | A | F | L |
| --- | --- | --- | --- |
| 2090 [1] | 774 | 100 | 200 |
| 2117 [2] | 774 | 100 | 50 |
| 2118 [3] | 1136 | 100 | 100 |
| 2295 [4] | >1470 | — | 100 |
| 1561 [7] | >1500 | 100 | 100 |
| 2080 [8] | 1470 | 100 | 400 |
| 2081 | >1470 | 200 | 100 |
| 2215 [9] | >1470 | 50 | 200 |

The results in Table 5 show that, with respect to the esters (Compounds Nos. 2117, 2118 and 2295) of 4α-hydroxy-8-methoxy-3-methyl-10-methylene-2,9-dioxatricyclo[4.3.1.0$^{3,7}$]decane (Compound No. 2090), the doses required to produce a lowering of the rectal temperature are smaller when the ester has the same or a lower toxicity, whereas, with respect to the esters (Compounds Nos. 2080, 2081 and 2215) of 4α-hydroxy-8-methoxy-3,10-dimethyl-2,9-dioxatricyclo[4.3.1.0$^{3,7}$]decane (Compound No. 1561), ptosis is produced with one-fourth or one-half of the dose required of the 4-hydroxy-compound.

A pharmaceutical composition incorporating the compounds of the invention as the active ingredients can be formed in conventional manner by using conventional carrier materials which are inert to the active components. The carrier materials may, for instance, be water, a pharmaceutically acceptable vegetable oil, gelatin, lactose, a polyethyleneglycol, starch, magnesium stearate, talcum, etc.

For parenteral application, solutions, preferably oily or aqueous solutions, may best be used. However, the compounds can also be administered in the form of suspensions or emulsions.

For enteral application, tablets, capsules or lozenges may be used which may contain the usual additives, for instance, preservatives, stabilizers, and wetting agents.

The compounds may be administered by mouth or by subcutaneous or intravenous injection.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A compound of the group consisting of esters of 4-hydroxy-2,9-dioxatricyclo[4.3.1.0³,⁷]decanes with carbamic acids having the formula

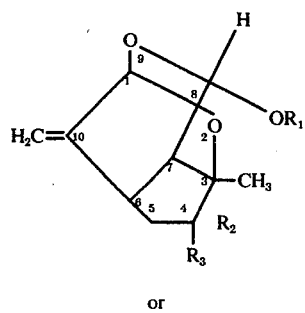

or

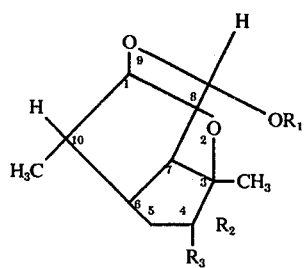

in which formulae $R_1$ is alkyl of at most 4 carbon atoms and one of $R_2$ and $R_3$ is hydrogen and the other is carbamyloxy having the formula —OCONHR, in which R is hydrogen, allyl, phenyl, cyclohexyl or alkyl of at most 4 carbon atoms.

2. The compound of claim 1 in which $R_2$ is hydrogen and $R_3$ is said carbamyloxy.

3. The compound of claim 1 in which $R_2$ is said carbamyloxy and $R_3$ is hydrogen.

4. A compound as defined in claim 1 which is 4α-(N-ethylcarbamyloxy)-8-methoxy-3-methyl-10-methylene-2,9-dioxatricyclo[4.3.1.0³,⁷]decane.

5. A compound as defined in claim 1 which is 4α-(N-n-propylcarbamyloxy)-8-methoxy-3-methyl-10-methylene-2,9-dioxatricyclo[4.3.1.0³,⁷]decane.

6. A compound as defined in claim 1 which is 4α-(N-isopropylcarbamyloxy)-8-methoxy-3-methyl-10-methylene-2,9-dioxatricyclo[4.3.1.1³,⁷]decane.

7. A compound as defined in claim 1 which is 4α-(N-cyclohexylcarbamyloxy)-8-methoxy-3-methyl-10-methylene-2,9-dioxatricyclo[4.3.1.0³,⁷]decane.

8. A compound as defined in claim 1 which is 4α-(N-allylcarbamyloxy)-8-methoxy-3-methyl-10-methylene-2,9-dioxatricyclo[4.3.1.0³,⁷]decane.

9. A compound as defined in claim 1 which is 4α-(N-ethylcarbamyloxy)-8-ethoxy-3-methyl-10-methylene-2,9-dioxatricyclo[4.3.1.0³,⁷]decane.

10. A compound as defined in claim 1 which is 4α-(N-ethylcarbamyloxy)-8-methoxy-3,10-dimethyl-2,9-cioxatricyclo[4.3.1.0³,⁷]decane.

11. A compound as defined in claim 1 which is 4α-(N-n-propylcarbamyloxy)-8-methoxy-3,10-dimethyl-2,9-dioxatricyclo[4.3.1.0³,⁷]decane.

12. A compound as defined in claim 1 which is 4α-(N-isopropylcarbamyloxy)-8-methoxy-3,10-dimethyl-2,9-dioxatricyclo[4.3.1.0³,⁷]decane.

13. A compound as defined in claim 1 which is 4α-(N-cyclohexylcarbamyloxy)-8-methoxy-3,10-dimethyl-2,9-dioxatricyclo[4.3.1.0³,⁷]decane.

14. A compound as defined in claim 1 which is 4α-(N-allylcarbamyloxy)-8-methoxy-3,10-dimethyl-2,9-dioxatricyclo[4.3.1.0³,⁷]decane.

15. A compound as defined in claim 1 which is 4α-(N-ethylcarbamyloxy-8-ethoxy-3,10-dimethyl-2,9-dioxatricyclo[4.3.1.0³,⁷]decane.

16. A compound as defined in claim 1 which is 4β-carbamyloxy-8-methoxy-3-methyl-10-methylene-2,9-dioxatricyclo[4.3.1.0³,⁷]decane.

17. A compound as defined in claim 1 which is 4β-(N-ethylcarbamyloxy)-8-methoxy-3-methyl-10-methylene-2,9-dioxatricyclo[4.3.1.0³,⁷]decane.

18. A compound as defined in claim 1 which is 4β-(N-allylcarbamyloxy)-8-methoxy-3-methyl-10-methylene-2,9-dioxatricyclo[4.3.1.0³,⁷]decane.

19. A compound as defined in claim 1 which is 4β-carbamoyloxy-8-methoxy-3,10-dimethyl-2,9-dioxatricyclo[4.3.1.0³,⁷]decane.

20. A compound as defined in claim 1 which is 4β-(N-ethylcarbamyloxy)-8-methoxy-3,10-dimethyl-2,9-dioxatricyclo[4.3.1.0³,⁷]decane.

21. A compound as defined in claim 1 which is 4β-(N-isopropylcarbamyloxy)-8-methoxy-3,10-dimethyl-2,9-dioxyatricyclo[4.3.1.0³,⁷]decane.

22. A compound as defined in claim 1 which is 4β-(N-phenylcarbamyloxy)-8-methoxy-3,10-dimethyl-2,9-dioxatricyclo[4.3.1.0³,⁷]decane.

* * * * *

UNITED STATES PATENT AND TRADEMARK OFFICE
CERTIFICATE OF CORRECTION

PATENT NO. : 4,016,176
DATED : April 5, 1977
INVENTOR(S) : PETER WILLIBRORD THIES It is certified that error appears in the above-identified patent and that said Letters Patent are hereby corrected as shown below:

In the Abstract, second drawing from top; column 1, lines 37-47; column 3, lines 40-49; column 11, Table 2, Example 17; column 13, Table 2, Example 17; column 17, claim 1, lines 23-33, change

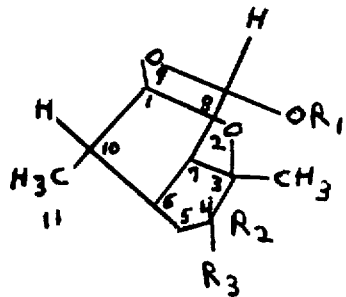 to 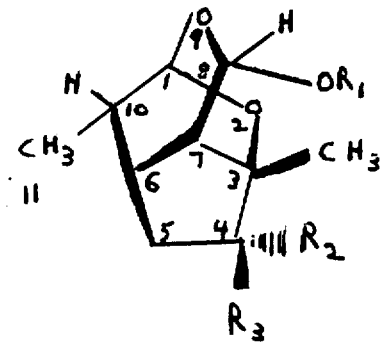

UNITED STATES PATENT AND TRADEMARK OFFICE
CERTIFICATE OF CORRECTION

PATENT NO. : 4,016,176
DATED : April 5, 1977
INVENTOR(S) : PETER WILLIBRORD THIES It is certified that error appears in the above-identified patent and that said Letters Patent are hereby corrected as shown below:

In the Abstract, first drawing from the top; in column 1, lines 26-36; column 3, lines 30-39; column 11; Table 1; Example 17; column 17 and claim 1, lines 11-21, change

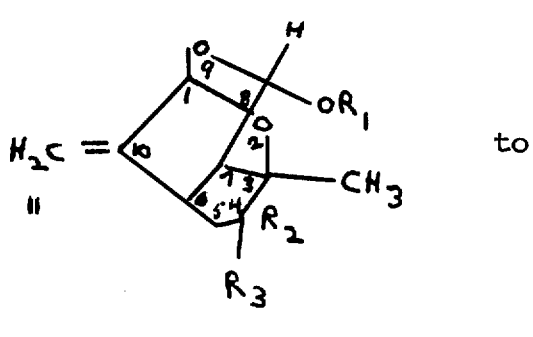 to 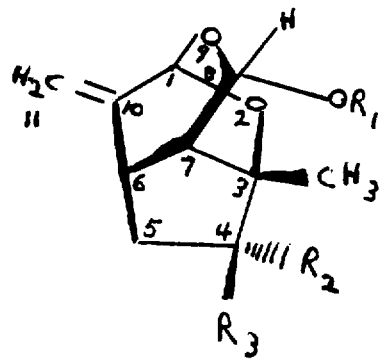

Signed and Sealed this

Thirteenth Day of December 1977

[SEAL]

Attest:

RUTH C. MASON
Attesting Officer

LUTRELLE F. PARKER
Acting Commissioner of Patents and Trademarks